(12) United States Patent
Hayashida et al.

(10) Patent No.: US 7,867,229 B2
(45) Date of Patent: Jan. 11, 2011

(54) HIGH-FREQUENCY TREATMENT APPARATUS

(75) Inventors: Tsuyoshi Hayashida, Sagamihara (JP); Kazunori Taniguchi, Hachioji (JP); Shigeo Nagayama, Hachioji (JP); Kazuya Hijii, Tama (JP)

(73) Assignee: Olympus Corporation, Tokyo (JP)

( * ) Notice: Subject to any disclaimer, the term of this patent is extended or adjusted under 35 U.S.C. 154(b) by 1090 days.

(21) Appl. No.: 11/601,183

(22) Filed: Nov. 17, 2006

(65) Prior Publication Data

US 2007/0066976 A1    Mar. 22, 2007

Related U.S. Application Data

(63) Continuation of application No. PCT/JP2005/018422, filed on Oct. 5, 2005.

(30) Foreign Application Priority Data

Oct. 5, 2004  (JP) .............................. 2004-292955

(51) Int. Cl.
    *A61B 18/14*  (2006.01)
(52) U.S. Cl. .......................................... 606/46; 606/45
(58) Field of Classification Search .............. 606/45–47
    See application file for complete search history.

(56) References Cited

U.S. PATENT DOCUMENTS

| 3,939,839 | A | * | 2/1976 | Curtiss ......................... | 606/46 |
| 4,726,370 | A | * | 2/1988 | Karasawa et al. ............. | 606/46 |
| 5,080,660 | A | * | 1/1992 | Buelna ......................... | 606/46 |
| 5,569,244 | A | * | 10/1996 | Hahnen ........................ | 606/46 |
| 5,749,870 | A | * | 5/1998 | Gloth et al. ................... | 606/45 |
| 5,919,190 | A | * | 7/1999 | VanDusseldorp ............ | 606/46 |
| 6,113,597 | A | * | 9/2000 | Eggers et al. ................. | 606/46 |
| 6,494,881 | B1 | * | 12/2002 | Bales et al. ................... | 606/45 |
| 6,939,348 | B2 | * | 9/2005 | Malecki et al. ............... | 606/41 |
| 7,662,151 | B2 | * | 2/2010 | Crompton et al. ............. | 606/41 |

(Continued)

FOREIGN PATENT DOCUMENTS

JP    09-262244    10/1997

(Continued)

OTHER PUBLICATIONS

Japanese Official Action dated Feb. 9, 2010.

*Primary Examiner*—Michael Peffley
(74) *Attorney, Agent, or Firm*—Scully, Scott, Murph7 & Presser, P.C.

(57) ABSTRACT

According to the present invention, a high-frequency treatment apparatus includes: an electrode assembly electrically connected to the high-frequency generating unit for generating a high-frequency current, the assembly having at the distal end thereof a current-applying electrode for discharging the high-frequency current, the proximal end of the current-applying electrode being covered with a first insulating member; an insertion section receiving the electrode assembly such that the electrode assembly is movable in predetermined directions, the insertion section being located on the return side of the high-frequency current applied from the current-applying electrode; a liquid supply unit for supplying an irrigation liquid to the vicinity of the current-applying electrode; and a second insulating member for covering a predetermined area on the surface of base part of the current-applying electrode, the base part being exposed from the distal end of the first insulating member.

9 Claims, 13 Drawing Sheets

U.S. PATENT DOCUMENTS

2004/0019351 A1  1/2004  Ohyama et al.
2004/0181216 A1  9/2004  Kelly et al.

FOREIGN PATENT DOCUMENTS

| | | |
|---|---|---|
| JP | 2000-201946 | 7/2000 |
| JP | 2001-095814 | 4/2001 |
| JP | 2001-517529 | 10/2001 |
| JP | 2002-514097 | 5/2002 |
| JP | 2003-305055 | 10/2003 |
| WO | WO 98/03117 | 1/1998 |
| WO | WO 99/16371 | 4/1999 |

* cited by examiner

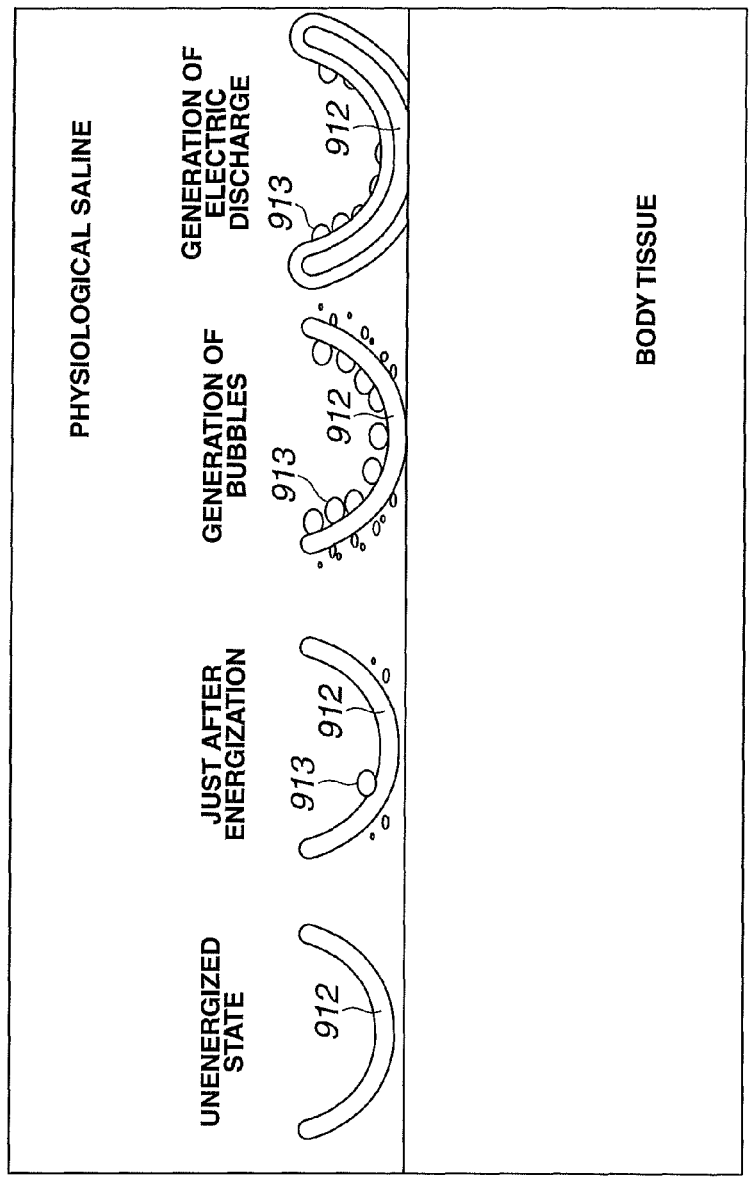

HIGH-FREQUENCY TREATMENT APPARATUS

CROSS REFERENCES TO RELATED APPLICATION

This application is a continuation application of PCT/JP2005/018422 filed on Oct. 5, 2005 and claims benefit of Japanese Application No. 2004-292955 filed in Japan on Oct. 5, 2004, the entire contents of which are incorporated herein by this reference.

BACKGROUND OF THE INVENTION

1. Field of the Invention

The present invention relates to a high-frequency treatment apparatus, used in an irrigation liquid, for performing electric surgery, such as resection, vaporization, or electric coagulation of body tissue.

2. Description of the Related Art

In the past resectoscope apparatuses have been included in high-frequency treatment apparatuses, used in an irrigation liquid, for performing electric surgery, such as resection, vaporization, or electric coagulation of body tissue.

A resectoscope apparatus, generally used for transurethral resection and transcervical resection, primarily includes an elongated hollow sheath to be inserted into the body cavity, a telescope, serving as an endoscope for observation, and an electrode unit for cauterization of body tissue, the telescope and electrode unit being disposed in the sheath.

During observing the body cavity using the resectoscope apparatus, a liquid is supplied through the sheath to the body cavity, thereby providing the field of vision of the endoscope.

In the past, as for the liquid supplied into the body cavity, D-Sorbitol, a nonconductive solution, has been used. A high-frequency current is supplied from an electrode to human body tissue and is then collected by a collector electrode arranged outside of the body.

In the conventional resectoscope apparatus, adductor contraction may be caused by stimulating a nerve through a high-frequency current. Accordingly, nerve block is needed. In addition, D-Sorbitol cannot be supplied into the body cavity for a long time. Unfortunately, time for surgical treatment is limited.

Japanese Unexamined Patent Application Publication No. 2000-201946 discloses a technique to overcome the above-described disadvantages. According to this technique, physiological saline is used as an irrigation liquid that can be supplied into the body cavity of a human being for a long time and a high-frequency current is collected by a sheath instead of a collector electrode, thus reducing nerve stimulation.

FIG. 14 is a diagram showing the structure of a conventional resectoscope apparatus using an irrigation liquid, such as physiological saline.

Referring to FIG. 14, a resectoscope apparatus 901 includes a resectoscope 902, a pack 903 of physiological saline, a liquid supply tube 904, a high-frequency power source 905, an electrode cable 906, and a footswitch 907.

A patient 909 lies on a surgical bed 908.

The distal end 911 of the resectoscope 902 is inserted into the urethra or the like of the patient 909. Referring to FIG. 15, the distal end 911 includes an electrode assembly 914 having an electrode 912 whose distal end part is shaped in a substantially semicircle. The electrode 912 of the electrode assembly 914 is covered with tube members 915 such that only the substantially semicircular distal end part is exposed.

Again referring to FIG. 14, the resectoscope 902 is supplied with physiological saline, serving as an irrigation liquid, from the pack 903 via the liquid supply tube 904. The resectoscope 902 is connected through the electrode cable 906 to the high-frequency power source 905.

When the footswitch 907 is pressed, the high-frequency power source 905 generates a high-frequency current and supplies the current through the electrode cable 906 to the electrode 912 arranged at the tip of the distal end 911 of the resectoscope apparatus 902.

FIG. 16 is a diagram explaining states of the vicinity of the electrode when a high-frequency current is supplied to the electrode 912 at the distal end 911 of the resectoscope 902.

As shown in FIG. 16, after starting of high-frequency current supply to the electrode 912 in an unenergized state, physiological saline is heated in the vicinity of the electrode 912 supplied with thermal energy through the electric impedance of the electrode 912, thus initiating the generation of bubbles 913.

The high-frequency current is further continuously supplied to the electrode 912, thus resulting in an increase of the amount of generated bubbles 913. Thus, the whole periphery of the electrode 912 is covered with the bubbles 913. At that time, the electrode impedance between the electrode 912 and the physiological saline steeply increases, so that a high voltage causes electric discharge. Resection, vaporization, or electric coagulation of body tissue can be achieved by heat generated by the electric discharge.

SUMMARY OF THE INVENTION

According to the present invention, there is provided a high-frequency treatment apparatus including: an electrode assembly electrically connected to the high-frequency generating unit for generating a high-frequency current, the assembly having at the distal end thereof a current-applying electrode for discharging the high-frequency current, the proximal end of the current-applying electrode being covered with a first insulating member; an insertion section receiving the electrode assembly such that the electrode assembly is movable in predetermined directions, the insertion section being located on the return side of the high-frequency current applied from the current-applying electrode; a liquid supply unit for supplying an irrigation liquid to the vicinity of the current-applying electrode; and a second insulating member for covering a predetermined area on the surface of base part of the current-applying electrode, the base part being exposed from the distal end of the first insulating member.

The present invention realizes a high-frequency treatment apparatus capable of achieving resection, vaporization, and electric coagulation of tissue in an irrigation liquid with less electric power and reducing time required for surgical treatment.

BRIEF DESCRIPTION OF THE DRAWINGS

FIG. 16 is a diagram explaining states of the vicinity of the electrode of the conventional resectoscope.

DESCRIPTION OF THE PREFERRED EMBODIMENTS

An embodiment of the present invention will now be described below with reference to FIGS. 1 to 7.

Figure 1:
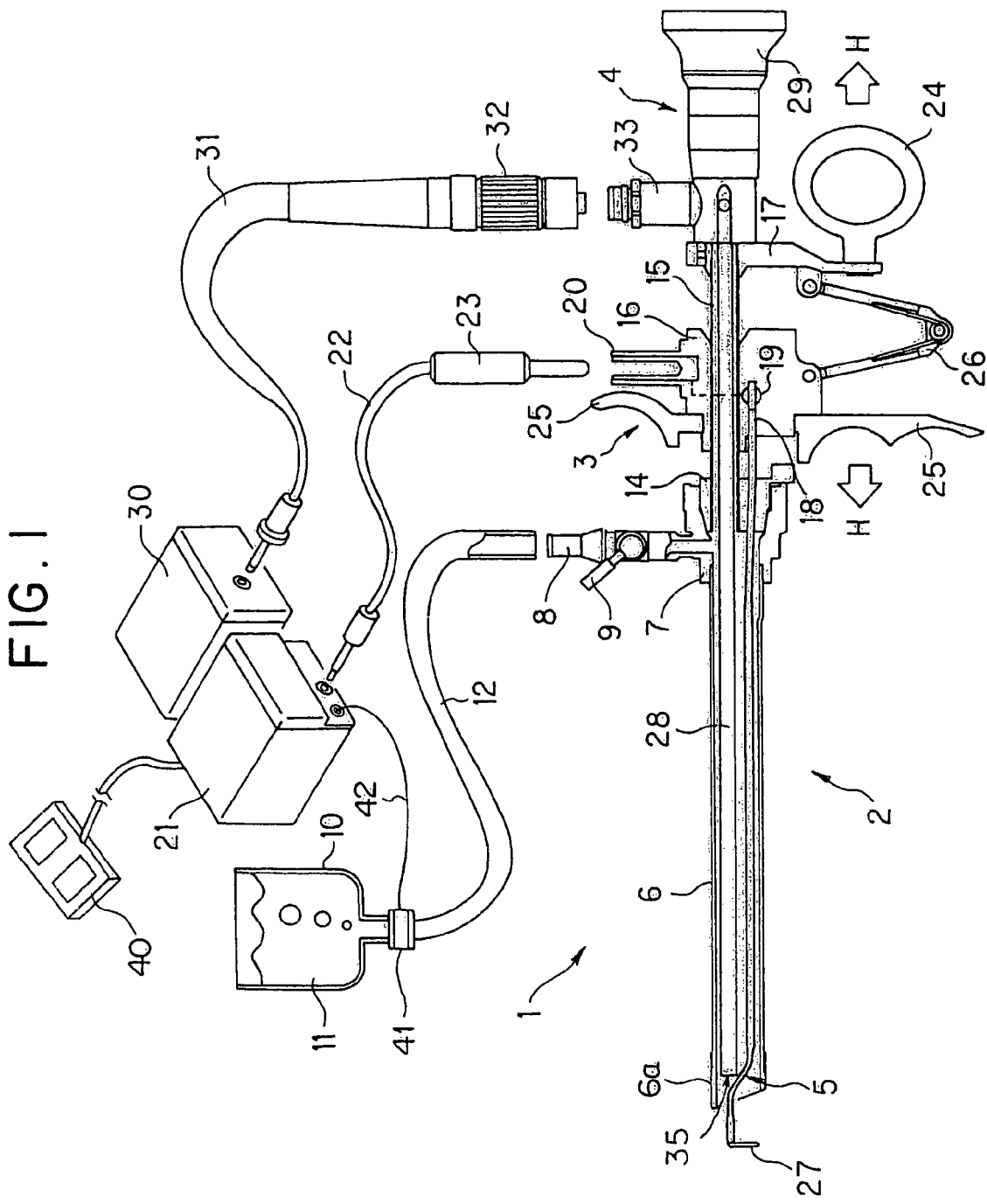
FIG. 1 is a diagram of the entire structure of a high-frequency treatment apparatus.
Figure 2:
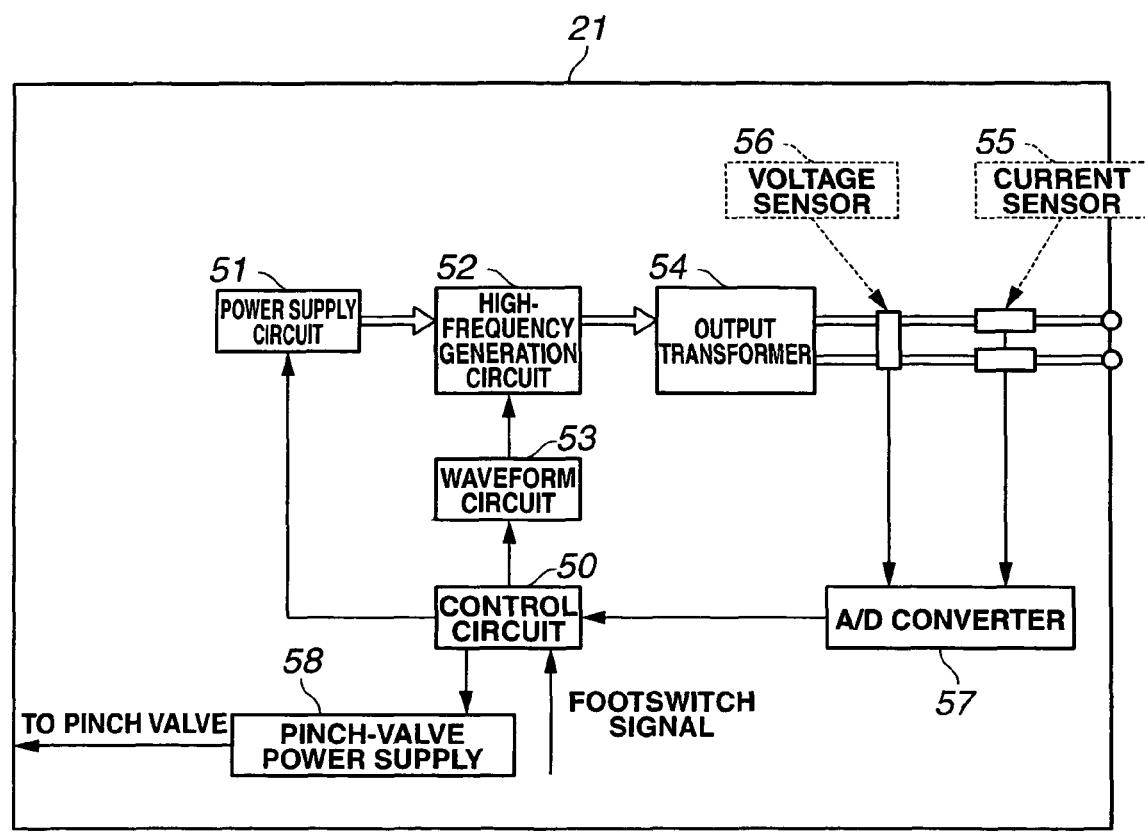
FIG. 2 is a block diagram of a high-frequency power supply unit.
Figure 3:
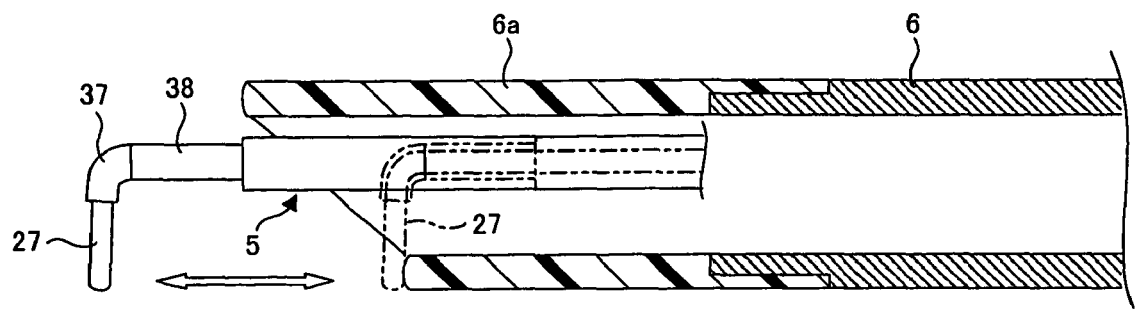
FIG. 3 is a sectional view showing distal end part of a resectoscope.
Figure 4:
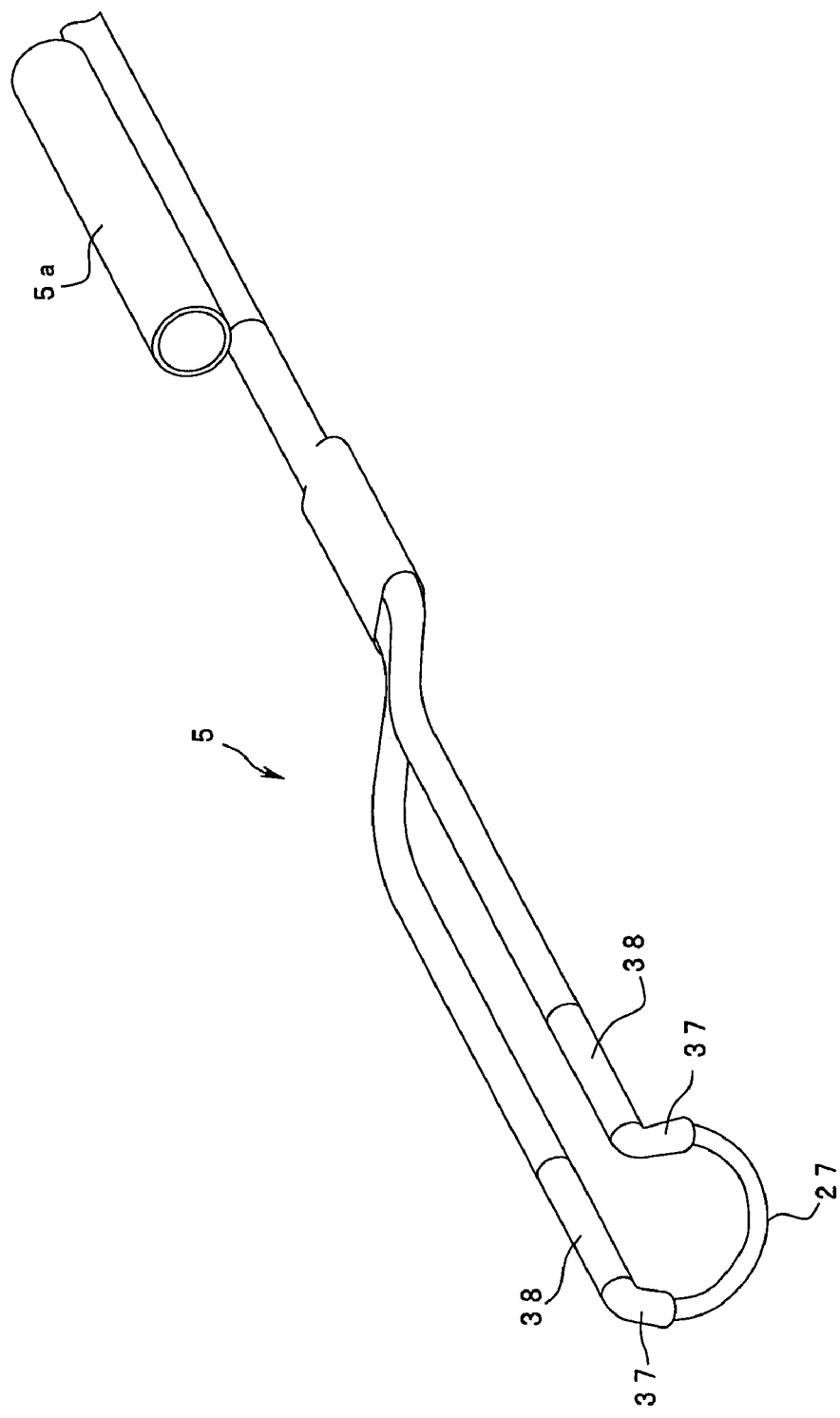
FIG. 4 is a diagram of the structure of an electrode assembly.
Figure 5:
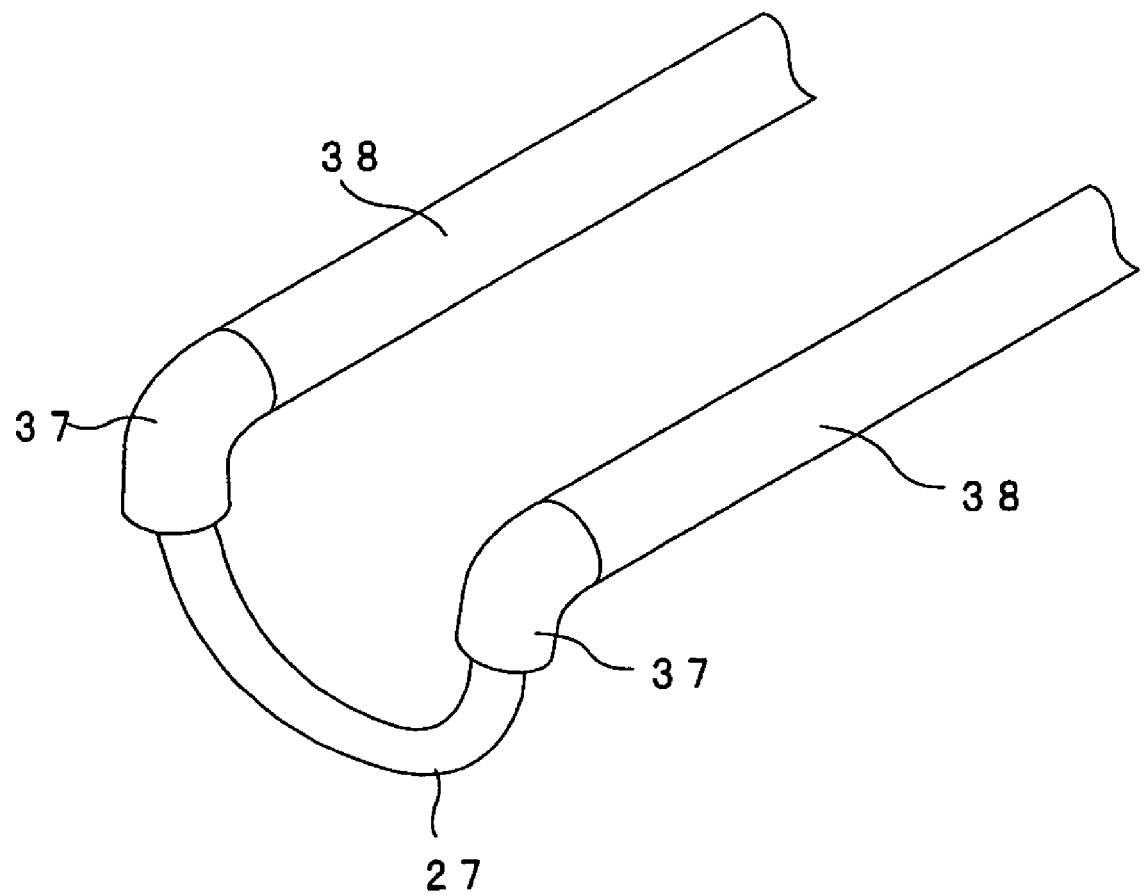
FIG. 5 is an enlarged view of distal end part of the electrode assembly.
Figure 6:
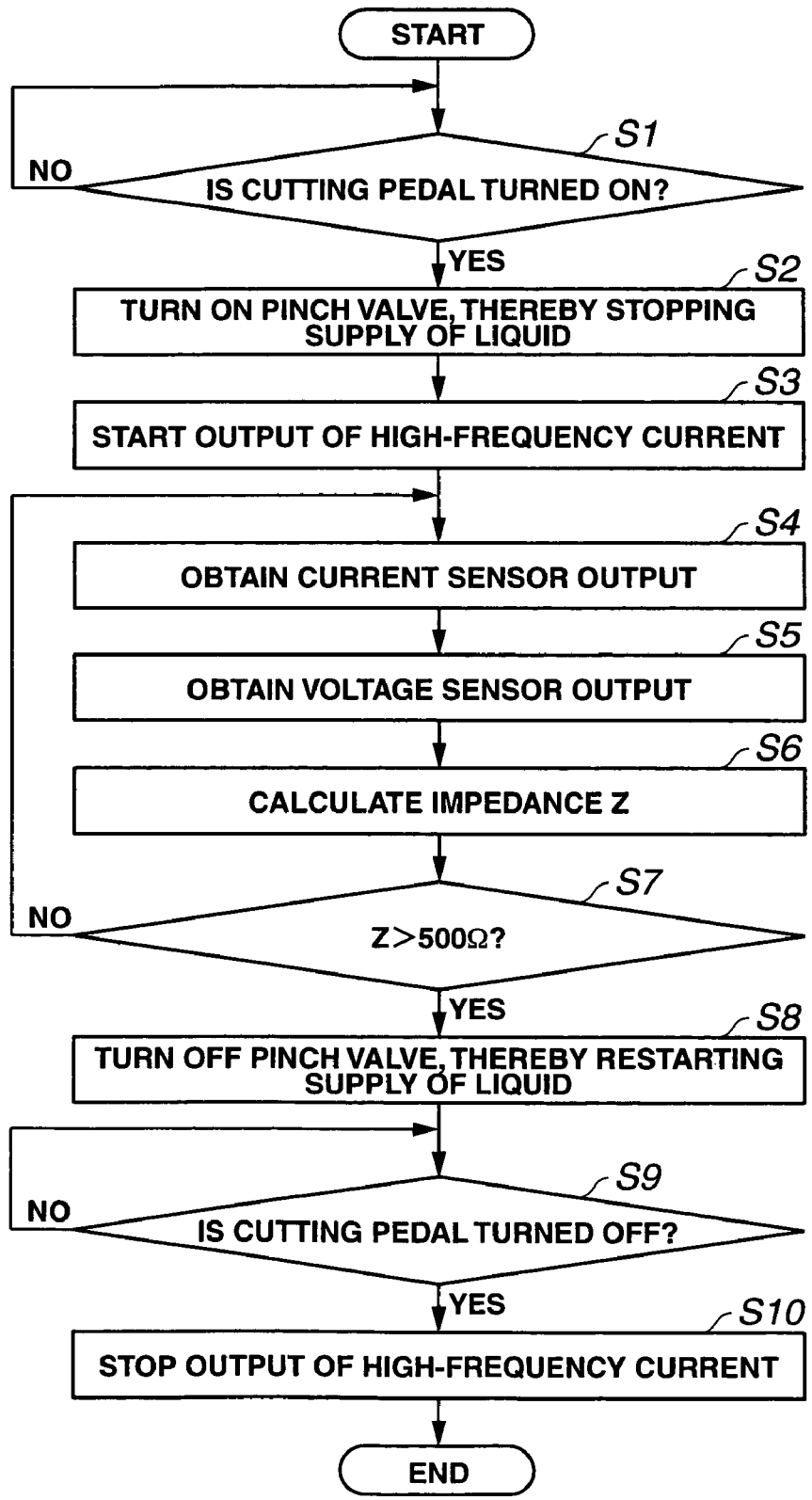
FIG. 6 is a flowchart showing control flow of the high-frequency power supply unit.
Figure 7:
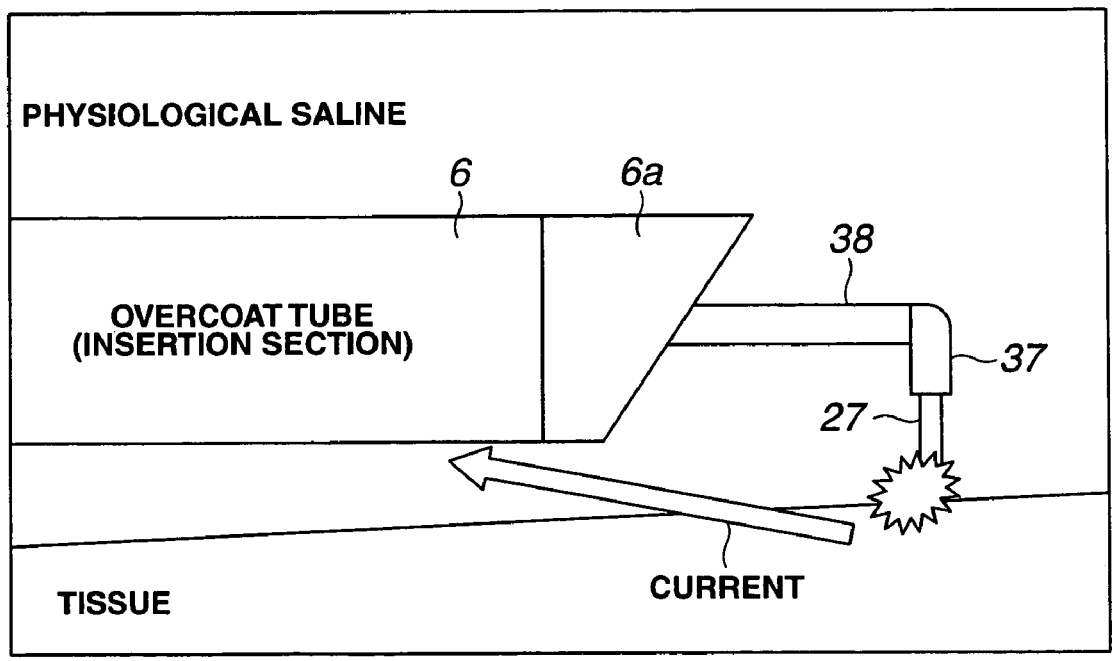
FIG. 7 is an enlarged view explaining the operation of the distal end part of the resectoscope.

FIGS. 1 to 7 relate to a first embodiment of the present invention. FIG. 1 is a diagram of the entire structure of a high-frequency treatment apparatus. FIG. 2 is a block diagram of a high-frequency power supply unit. FIG. 3 is a sectional view showing distal end part of a resectoscope. FIG. 4 is a diagram of the structure of an electrode assembly. FIG. 5 is an enlarged view of distal end part of the electrode assembly. FIG. 6 is a flowchart showing control flow of the high-frequency power supply unit. FIG. 7 is an enlarged view of the distal end part of the resectoscope to explain the operation thereof.

Referring to FIG. 1, a resectoscope 1, serving as a high-frequency treatment apparatus, primarily includes a tubular sheath 2, an operation section 3 provided on the proximal end of the sheath 2, a telescope 4 which is inserted through the operation section 3 into the sheath 2 and is used for observation, a high-frequency power supply unit 21, serving as a high-frequency generating unit, and an electrode assembly 5 which is supplied with a high-frequency current from the high-frequency power supply unit 21 used for treatment of body tissue.

The sheath 2 is inserted into the body cavity of a subject through the urethra or vagina thereof. The sheath 2 includes a distal end portion 6a, a conductive insertion section 6, and a body 7 provided on the rear of the insertion section 6. The body 7 includes an outlet 8 through which an irrigation liquid, e.g., physiological saline in the present embodiment, is supplied to the body cavity via the insertion section 6, the outlet 8 being provided with a cock 9. The outlet 8 is designed such that a liquid supply tube 12 for supplying physiological saline 11 in a pack 10 is detachably connectable to the outlet 8.

On the other hand, the operation section 3 includes an operation-section body 14, a guide shaft 15, and a slider 16. The operation-section body 14 is detachable from the rear end of the body 7 of the sheath 2. The guide shaft 15 projects from the rear end of the operation-section body 14. The slider 16 is slidably supported by the guide shaft 15.

A stopper 17 is provided for the rear end of the guide shaft 15. The slider 16 is slidable along the guide shaft 15 between the stopper 17 and the operation-section body 14. The guide shaft 15 is hollow. The telescope 4 is inserted into the sheath 2 through the guide shaft 15 and is detachably fixed to the stopper 17.

A holder 18 for holding the electrode assembly 5 and an electrical connection unit 19 for supplying a high-frequency current to the electrode assembly 5 are provided for the slider 16. The electrical connection unit 19 is electrically connected to a connector 20 provided for the slider 16. An output plug 23 is arranged at the distal end of an output cord 22 of the high-frequency power supply unit 21. The output plug 23 is detachably fixable to the connector 20.

The high-frequency power supply unit 21 is connected to a footswitch 40 having selector pedals for controlling the operation of supplying a high-frequency current to the electrode assembly 5 and controlling the output level of high-frequency current. A signal cable 42 extends from the front surface of the high-frequency power supply unit 21 such that one end of the signal cable 42 is connected thereto. The other end of the signal cable 42 is connected to a pinch valve 41 which couples the pack 10 to the liquid supply tube 12. In other words, the pinch valve 41 is supplied with power through the signal cable 42 from the high-frequency power supply unit 21.

The pack 10, the liquid supply tube 12, and the pinch valve 41 constitute a liquid supply unit.

The stopper 17 includes a handle 24 into which a user's thumb is inserted. On the other, the slider 16 includes a handle 25 on which the user places their fingers, e.g., the index to ring or little fingers. The handles 24 and 25 are connected through a spring-loaded joint 26 such that they are biased by the spring-loaded joint 26 in the directions shown by arrows H.

When the handles 24 and 25 are operated to slide the slider 16 along the guide shaft 15 toward the operation-section body 14 (i.e., forwardly), a distal-end electrode 27 of the electrode assembly 5 is projected from the distal end of the sheath 2. When the slider 16 is moved toward the stopper (i.e., backwardly), the distal-end electrode 27 of the electrode assembly 5 is received in the distal end portion 6a of the sheath 2.

The telescope 4 includes an insertion section 28 inserted into the sheath 2 and an eyepiece 29 disposed at the rear end of the insertion section 28. A light guide connector 33 is arranged in the vicinity of the eyepiece 29. A connector 32 of a light guide cable 31 connected to a light source unit 30 is detachably fixable to the light guide connector 33.

Illumination light emitted from the light source unit 30 is transmitted through the light guide cable 31 to the light guide connector 33 and is further transmitted through a light guide bundle disposed in the insertion section 28 to the distal end 35 of the insertion section, so that the light is released.

Referring to FIG. 2, the high-frequency power supply unit 21, serving as a high-frequency generating unit, includes a control circuit 50, a power supply circuit 51, a high-frequency generation circuit 52, a waveform circuit 53, an output transformer 54, a current sensor 55, a voltage sensor 56, an analog-to-digital (A/D) converter 57, and a pinch-valve power supply 58.

The power supply circuit 51 outputs a direct current. The high-frequency generation circuit 52 converts the direct current supplied from the power supply circuit 51 into a high-frequency current. The waveform circuit 53 designates the shape of high-frequency current to the high-frequency generation circuit 52 under the control of the control circuit 50.

The output transformer 54 outputs the high-frequency current supplied from the high-frequency generation circuit 52 to wires in the output cord 22 connected to the resectoscope 1. The current sensor 55 detects an output current output from the output transformer 54.

The voltage sensor 56 detects an output voltage output from the output transformer 54. The A/D converter 57 converts signals output from the current sensor 55 and the voltage sensor 56 into digital signal data. The control circuit 50 controls the power supply circuit 51 and the waveform circuit 53 on the basis of the digital data supplied from the A/D converter 57 and a signal supplied from the footswitch 40. In addition, the control circuit 50 controls the pinch-valve power supply 58 for supplying power to the pinch valve 41.

The electrode assembly 5 to be projected from or received into the distal end portion 6a of the sheath 2 of the resectoscope 1 will now be described with reference to FIGS. 3 to 5.

Referring to FIG. 3, the distal-end electrode 27, serving as functional part of the electrode assembly 5, is exposed from the distal end portion 6a of the resectoscope 1. The distal-end electrode 27 is bent in a substantially L-shaped as viewed from the side so that the distal-end electrode 27 is easily contactable with tissue. As mentioned above, the electrode assembly 5 is slidable in such a manner that when the handles 24 and 25 (see FIG. 1) are operated, the distal end part including the distal-end electrode 27 is projected forward from the distal end portion 6a of the resectoscope 1, alternatively, the distal end part is substantially received into the distal end portion 6a.

Referring to FIG. 4, the distal end part of the electrode assembly 5 is branched into two segments. The distal-end electrode, 27, made of a metal wire shaped in a substantially loop (closed loop) serving as a current-applying electrode, is arranged such as to interconnect ends of the two branched segments. A sleeve 38, serving as a first (electrical) insulating member, is arranged on the distal end of each branched segment of the electrode assembly 5.

A guide tube 5a is fixed to an upper portion, as viewed in FIG. 4, of the distal-end electrode 27 such that the guide tube 5a is positioned between the branch point of the electrode assembly 5 and the proximal end. The insertion section 28 of the telescope 4 is inserted through the guide tube 5a. Accordingly, when being slid, the electrode assembly 5 is guided straight by the guide tube 5a through which the insertion section 28 of the telescope 4 is inserted.

As shown in FIGS. 4 and 5, two insulating members (second insulating members in the present embodiment) 37 extend downwardly in the drawings, i.e., vertically from the distal ends of the respective sleeves 38. Predetermined areas on the surface of the distal-end electrode 27 are covered with the insulating members 37. More specifically, the insulating members 37 cover the predetermined areas on respective base parts of the distal-end electrode 27. The base parts of the distal-end electrode 27 extend from the two branched segments of the electrode assembly 5, respectively. In other words, since the base parts are exposed from the distal ends of the sleeves 38 and are not often used during resection, vaporization, or electric coagulation of tissue, only the predetermined areas on the base parts of the distal-end electrode 27 are covered with the two insulating members 37.

The sleeves 38 and the insulating members 27 are arranged on the electrode assembly 5 so that the distal-end electrode 27, made of a metal wire, serves as a contact portion to be come into contact with a target treatment region in the body cavity and other portions excluding the contact portion serve as non-contact portions kept from contact with the target treatment region. In the electrode assembly 5, a portion covered with each sleeve 38 corresponds to a first portion. Since the base parts of the distal-end electrode 27 extend from the respective first portions in the direction different from the axes of the first portions, the base parts are bent. The distal-end electrode 27 serves as a second portion of the electrode assembly 5. The insulating members 37 cover the bent portions as the base parts of the distal-end electrode 27.

The operation of the resectoscope with the above-described structure according to the present embodiment will now be described below with reference to FIGS. 6 and 7.

First, the resectoscope 1 is inserted into the body cavity of a patient through, e.g., the urethra or vagina or the like, thereof.

Referring to FIG. 6, a pedal for cutting (hereinafter, cutting pedal) of the footswitch 40 is pressed, i.e., turned on (S1). The control circuit 50 controls the pinch-valve power supply 58 to supply power to the pinch valve 41, thereby temporarily interrupting the supply of physiological saline through the liquid supply tube 12 (S2). The control circuit 50 controls the high-frequency generation circuit 52 to start the supply of a high-frequency current (S3).

At that time, since the supply of physiological saline is stopped, physiological saline heated by the high-frequency current is remained in the vicinity of the distal-end electrode 27, so that bubbles are easily generated. In addition, since the supply of physiological saline is temporarily interrupted, the generated bubbles are not scattered by supplying the liquid. As shown in FIG. 7, the high-frequency current, supplied to the distal-end electrode 27, flows from the contact portion of the distal-end electrode 27, serving as a current-applying electrode, to the insertion section 6 located on the return side, the contact portion being in contact with body tissue. Consequently, the tissue in contact with the distal-end electrode 27 is subjected to resection, vaporization, or electric coagulation.

Figure 15:
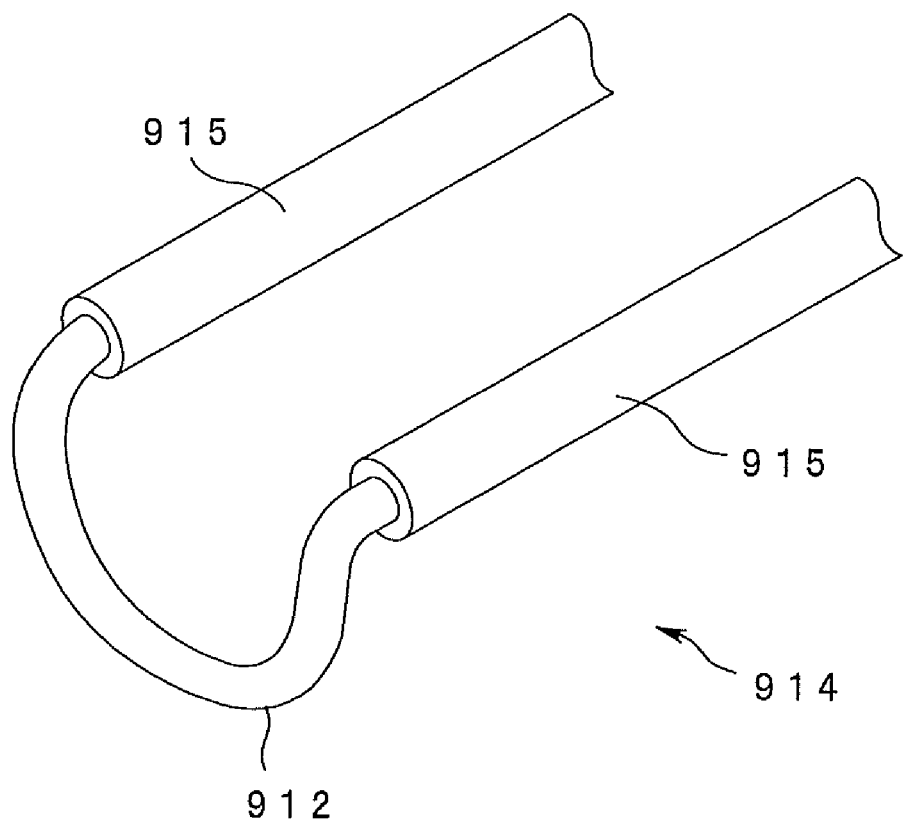
FIG. 15 is a diagram showing a conventional electrode.

Since the base parts of the distal-end electrode 27 are covered with the insulating members 37, the surface area of the distal-end electrode 27 in contact with physiological saline is smaller than that of the conventional electrode 912 (refer to FIG. 15). Advantageously, the temperature of physiological saline can be increased with higher efficiency. Therefore, bubbles are easily generated on the periphery of the exposed distal-end electrode 27.

After that, the control circuit 50 acquires a current value of the current sensor 55 through the A/D converter 57 in step S4 and then obtains a voltage value of the voltage sensor 56 therethrough in step S5.

The control circuit 50 divides the obtained voltage value by the obtained current value to obtain an impedance value Z between the distal-end electrode 27 and the insertion section 6, serving as an overcoat tube.

Next, the control circuit 50 then determines whether the calculated impedance value Z is less than, e.g., 500Ω (S7). If the impedance value Z is less than 500Ω, the process is returned to step S4 and the control circuit 50 repeats step 4 and the subsequent steps.

On the other hand, when the calculated impedance value Z is larger than 500Ω, the whole periphery of the distal-end electrode 27 is covered by bubbles. Since electric discharge has already been generated, it is not necessary to interrupt the supply of physiological saline. The control circuit 50 turns off the power supply to the pinch valve 41 (S8), so that the supply of physiological saline to the vicinity of the distal-end electrode 27 is restarted.

When the cutting pedal of the footswitch 40 is turned off (S9), the control circuit 50 controls the high-frequency generation circuit 52 to stop the output of high-frequency current (S10).

In other words, as mentioned above, when the cutting pedal of the footswitch 40 is turned on, bubbles are generated on the distal-end electrode 27. However, just after the cutting pedal of the footswitch 40 is turned on, bubbles are poorly generated on the distal-end electrode 27 because it takes time to increase the temperature of physiological saline. At that time, the impedance value Z of tissue impedance is lower than 500Ω. The control circuit 50 turns on the power supply to the pinch valve 41 and interrupts the supply of physiological saline to the vicinity of the distal-end electrode 27 through the liquid supply tube 12.

After a predetermined lapse of time from the turn-on of the cutting pedal of the footswitch 40, the amount of bubbles on the distal-end electrode 27 is increased, thus resulting in an increase in the impedance value Z. When the impedance value Z equals 500Ω, the whole periphery of the distal-end electrode 27 is covered with bubbles, electric discharge is generated, the power supply to the pinch valve 41 is turned off, and the supply of physiological saline to the vicinity of the distal-end electrode 27 through the liquid supply tube 12 is restarted.

Figure 14:
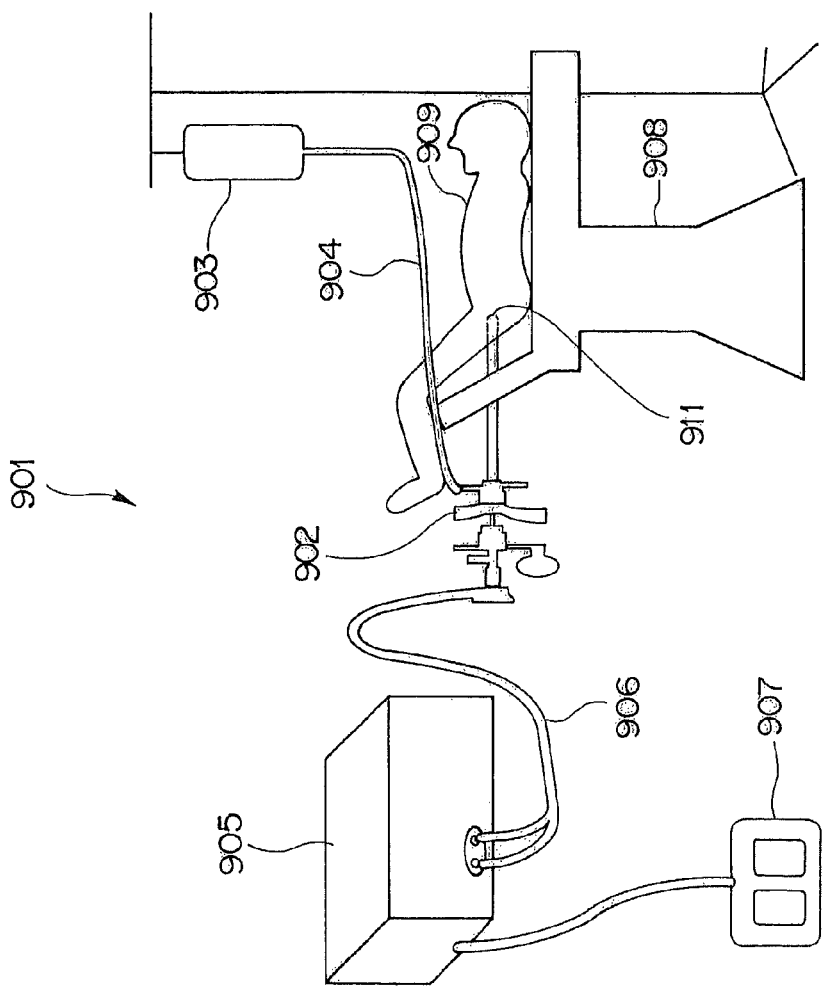
FIG. 14 is a diagram showing the structure of a high-frequency treatment apparatus including a conventional resectoscope using an irrigation liquid, such as physiological saline.

According to the present embodiment, as compared with the surface area of the electrode 912 provided for the conventional resectoscope apparatus 901 shown in FIGS. 14 to 16, the surface area of the distal-end electrode 27 in contact with physiological saline is reduced by the insulating members 37 for covering. Consequently, the time required to increase the temperature of physiological saline can be reduced. In other words, the resectoscope 1 according to the present embodiment is designed so as to reduce the time required to generate bubbles covering the whole periphery of the distal-end electrode 27 after the turn-on of the cutting pedal of the footswitch 40.

In the resectoscope 1 with the above-described structure according to the present embodiment, the time required to cover the whole periphery of the distal-end electrode 27 with bubbles after starting of high-frequency current output by the high-frequency power supply unit 21 can be reduced, the covering with bubbles being needed to generate electric discharge between the distal-end electrode 27 and the insertion section 6. In other words, since the surface area of the distal-end electrode 27 in contact with physiological saline is reduced by the insulating members 37, the time required to increase the temperature of physiological saline in the vicinity of the distal-end electrode 27 can be reduced.

Advantageously, in the resectoscope 1 according to the present embodiment, electric power saving effect can be obtained by reducing the time during which the high-frequency power supply unit 21 outputs a high-frequency current. In addition, bubbles to cover the whole periphery of the distal-end electrode 27 can be easily generated.

Further, since bubbles in the vicinity of the distal-end electrode 27 are not scattered due to the supply of liquid, the whole of the distal-end electrode 27 is covered with bubbles to generate electric discharge by low electric power, so that resection, vaporization, or electric coagulation of body tissue can be achieved.

Consequently, the high-frequency power supply unit 21 with low electric power can be used. Thus, a reduction in manufacturing cost of the resectoscope 1, serving as a high-frequency treatment apparatus, can be reduced and electric power can be saved.

In order to reduce the contact area of the distal-end electrode 27 with physiological saline as compared to that of the conventional electrode 912 (see FIG. 15), the distal-end electrode 27 may be provided with the following components shown in FIGS. 8 to 13 instead of the insulating members 37 covering the base parts of the distal-end electrode 27, the base parts being not often used during resection, vaporization, or electric coagulation and being exposed from the distal ends of the sleeves 38.

Figure 8:
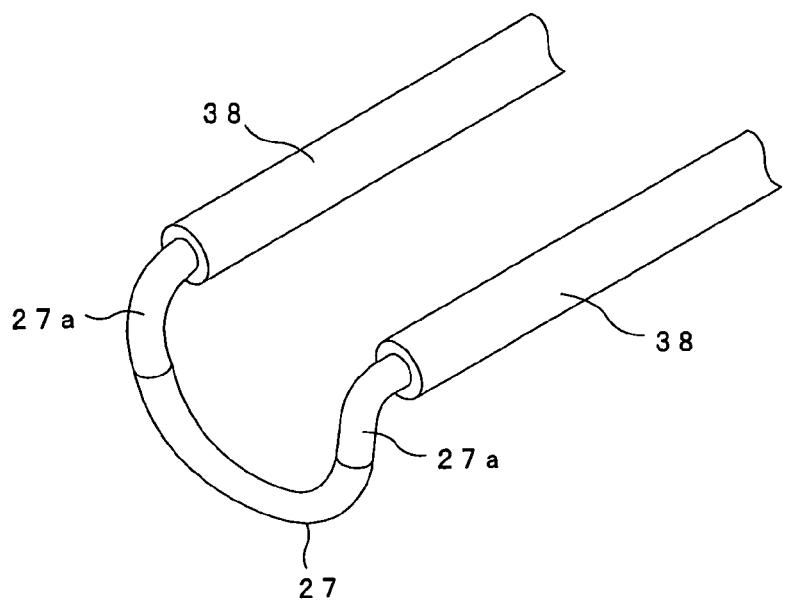
FIG. 8 is a diagram explaining a distal-end electrode arranged in the distal end part of the electrode assembly.

FIG. 8 shows another distal-end electrode 27 in which a predetermined area on the external surface of each base part (bent portion) exposed from the distal end of each sleeve 38 is covered with insulating coating 27a, made of a nonconductive film, serving as the second insulating member. Thus, the contact area of the distal-end electrode 27 with physiological saline is reduced.

Figure 9:
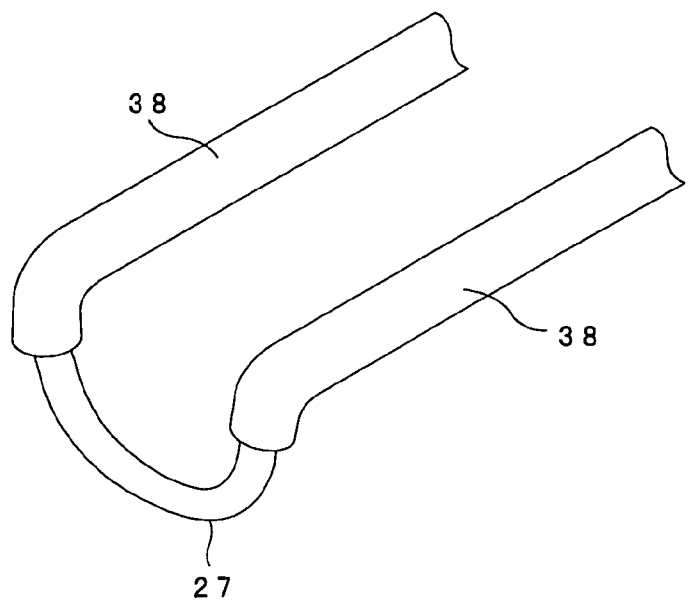
FIG. 9 is a diagram explaining a distal-end electrode arranged in the distal end part of the electrode assembly.

FIG. 9 shows another distal-end electrode 27 in which a predetermined area on the external surface of each base part (bent portion) is covered with distal end part, serving as the second insulating member, of each sleeve 38 such that the distal end part extends in the direction in which the corresponding base part extends. Thus, the contact area of the distal-end electrode 27 with physiological saline is reduced. In FIG. 9, the distal end part of each sleeve 38 is formed in a substantially L-shape such that the distal end part is bent downward, i.e., vertically.

Figure 10:
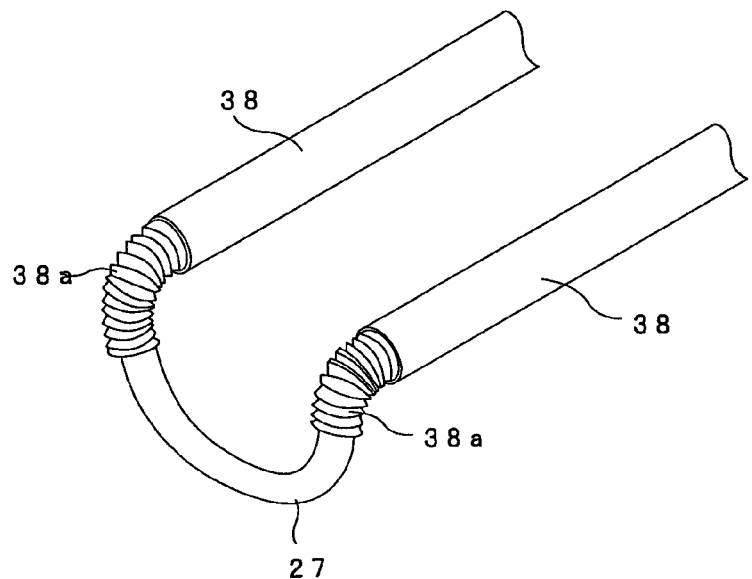
FIG. 10 is a diagram explaining a distal-end electrode arranged in the distal end part of the electrode assembly.

FIG. 10 shows another distal-end electrode 27 in which the external surface of each base part (bent portion) exposed from the distal end of each sleeve 38 is covered with a corrugated tube 38a (second insulating member according to the present embodiment), made of an insulating material such that the desired range to be covered can be changed. Thus, a user, such as a doctor, can reduce the contact area of the distal-end electrode 27 with physiological saline in the desired range.

In each of the distal-end electrodes 27 with the above-described structures shown in FIGS. 8 to 10, the time required to increase the temperature of physiological saline can be reduced, so that bubbles are easily generated on the periphery of the distal-end electrode 27. In addition, since the exposed area of the external surface of the distal-end electrode 27 is small, electric discharge from the distal-end electrode 27 to the insertion section 6 can be generated by a small amount of bubbles.

Further, in the distal-end electrode 27 with the structure shown in FIG. 10, the user, such as a doctor, can properly select the size of an exposed area of the distal-end electrode 27 in accordance with conditions of a patient undergoing treatment.

Figure 11:
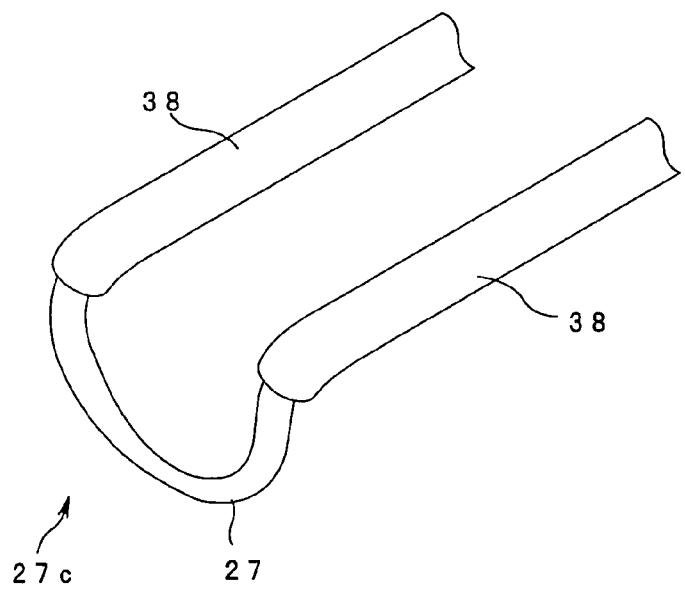
FIG. 11 is a diagram explaining a distal-end electrode arranged in the distal end part of the electrode assembly.

FIG. 11 shows another distal-end electrode 27 in which the outer diameter of loop-shaped middle part 27c, which is the most often used, is formed smaller than that of each base part exposed from the distal end of the corresponding sleeve 38. Since the outer diameter of the middle part 27c is small, the contact area of the distal-end electrode 27 with physiological saline is reduced. Thus, the periphery of the middle part 27c is sufficiently covered with a small amount of bubbles.

Figure 12:
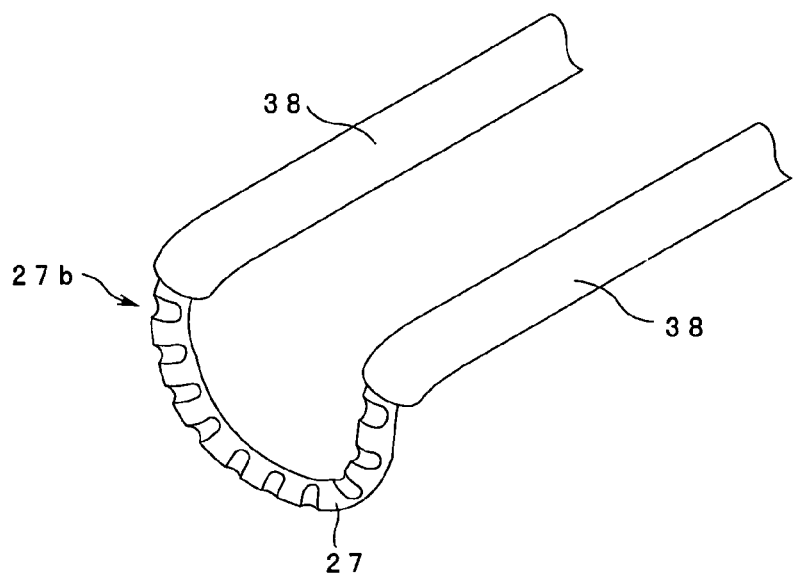
FIG. 12 is a diagram explaining a distal-end electrode arranged in the distal end part of the electrode assembly.

FIG. 12 shows another distal-end electrode 27 which includes a plurality of notches 27b on the front surface using the same principle as that in the distal-end electrode 27 shown in FIG. 11. The total contact area of the notches 27b with physiological saline is reduced. Therefore, the peripheries of the notches 27b are sufficiently covered with a small amount of bubbles.

Figure 13:
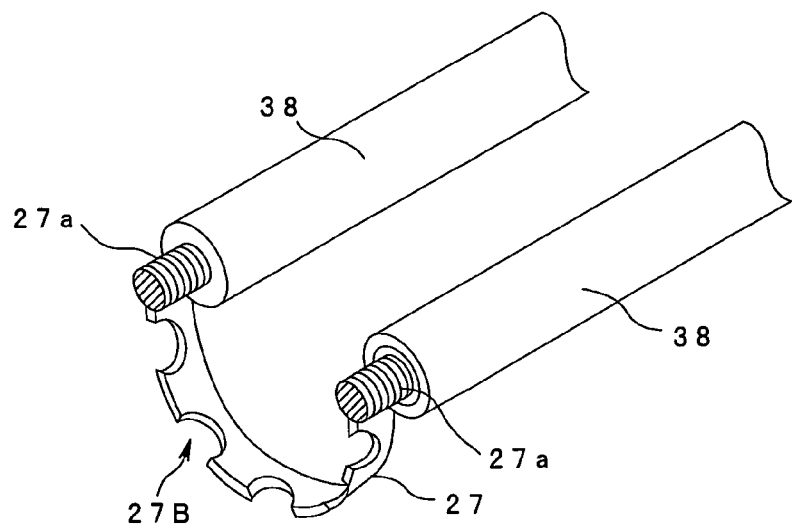
FIG. 13 is a diagram explaining a distal-end electrode arranged in the distal end part of the electrode assembly.

FIG. 13 shows another distal-end electrode 27 which is a loop (closed-loop) shaped plate having a plurality of notches 27B on the front surface. Thus, the above-described advantages can be obtained. Each base part of the plate-shaped distal-end electrode 27 is covered with the above-described insulating coating 27a, serving as the second insulating member.

In the above-described resectoscope 1 according to the present embodiment, since electric discharge is effectively generated between the distal-end electrode 27 and the insertion section 6 by a small amount of generated bubbles while the distal-end electrode 27 is being in contact with tissue, the power consumption of the high-frequency power supply unit 21 can be reduced and high-frequency electric power to be used can be realized with a small amount of power. Accordingly, an expensive high-frequency power supply unit 21 capable of outputting a large amount of power is not needed. An inexpensive high-frequency power supply unit 21 capable of immediately generating electric discharge between the distal-end electrode 27 and the insertion section 6 by a small amount of power while the distal-end electrode 27 is in contact with tissue can be used.

In the resectoscope 1 according to the present embodiment, since the time required to generate electric discharge can be reduced, the time required for surgical treatment can be reduced. Advantageously, burdens on the patient can also be reduced.

It should be understood that the present invention is not limited to the above-described embodiments and various changes and modifications thereof could be made without departing from the spirit or scope of the invention.

What is claimed is:

1. A high-frequency treatment apparatus comprising:
   an electrode assembly electrically connected to a high-frequency generating unit for generating a high-frequency current, the assembly having at a distal end thereof a current-applying electrode for discharging the high-frequency current, a proximal end of the current-applying electrode being covered with a first insulating member;
   an insertion section receiving the electrode assembly such that the electrode assembly is movable in predetermined directions;
   a liquid supply unit for supplying an irrigation liquid to a vicinity of the current-applying electrode through the insertion section; and
   a second insulating member for covering a base part of the current-applying electrode, the base part being exposed from a distal end of the first insulating member, such that a predetermined area on an external surface of the current-applying electrode is covered in a continuous manner from the first insulating member, the second insulating member being a separated body from the first insulating member and made of a corrugated tube-shaped extendable member configured to change a range of the predetermined area to be covered.

2. The apparatus according to claim 1, wherein the current-applying electrode is formed in a loop shape at distal end part such that the outer diameter of a middle part of the loop-shaped electrode is smaller than that of base part exposed from the distal end of the first insulating member.

3. The apparatus according to claim 2, wherein the current-applying electrode includes a plurality of notches.

4. The apparatus according to claim 1, wherein the current-applying electrode includes a plurality of notches.

5. The apparatus according to claim 1, wherein
   the current-applying electrode includes a contact portion to come into contact with a desired treatment region in a subject and a non-contact portion connecting to the first insulating member, and
   a predetermined area on at least part of the non-contact portion is covered with the second insulating member.

6. The apparatus according to claim 5, wherein
   the current-applying electrode includes a functional portion to perform a predetermined treatment to the subject and a non-functional portion, and
   at least part of the non-functional portion is covered with the first insulating member or the second insulating member.

7. The apparatus according to claim 1, wherein the current-applying electrode includes first parts, each of which the first insulating member is disposed on, extending in a predetermined direction in which the electrode assembly moves and a second part extending in a direction different from the extending direction of the first parts.

8. The apparatus according to claim 7, further comprising bent portions for connecting the first parts and the second part.

9. The apparatus according to claim 8, wherein the bent portions are covered with the second insulating members, respectively.

* * * * *